United States Patent
Hedden et al.

(10) Patent No.: US 9,040,731 B2
(45) Date of Patent: May 26, 2015

(54) METHOD FOR PREPARATION OF PLATINUM-CARBONYL-SILOXANE COMPOUNDS

(75) Inventors: Gregory Hedden, Flemington, NJ (US); Eric L. Frueh, Piscataway, NJ (US); Wayne J. Gallagher, Flemington, NJ (US)

(73) Assignee: Umicore AG & Co. KG, Hanau-Wolfgang (DE)

( * ) Notice: Subject to any disclaimer, the term of this patent is extended or adjusted under 35 U.S.C. 154(b) by 0 days.

(21) Appl. No.: 14/236,573

(22) PCT Filed: Jul. 31, 2012

(86) PCT No.: PCT/EP2012/064954
§ 371 (c)(1),
(2), (4) Date: Mar. 27, 2014

(87) PCT Pub. No.: WO2013/017593
PCT Pub. Date: Feb. 7, 2013

(65) Prior Publication Data
US 2014/0249281 A1 Sep. 4, 2014

Related U.S. Application Data

(60) Provisional application No. 61/513,800, filed on Aug. 1, 2011.

(51) Int. Cl.
| | | |
|---|---|---|
| *C07F 15/00* | (2006.01) | |
| *C08G 77/04* | (2006.01) | |
| *C08L 83/04* | (2006.01) | |
| *C08G 77/08* | (2006.01) | |
| *C08K 5/56* | (2006.01) | |

(52) U.S. Cl.
CPC ............ *C07F 15/0086* (2013.01); *C08G 77/08* (2013.01); *C08K 5/56* (2013.01); *C08L 83/04* (2013.01)

(58) Field of Classification Search
CPC ..... C07F 15/0086; C07F 19/00; C08G 77/08; C08L 83/04; C08K 5/56
USPC ........................ 556/9; 526/118, 126; 502/152
See application file for complete search history.

(56) References Cited

U.S. PATENT DOCUMENTS 3,865,858 A    2/1975   Ossko et al.

FOREIGN PATENT DOCUMENTS

| JP | 11-152337 A | * 11/1997 |
|---|---|---|
| JP | 2002 030185 A | 1/2002 |

OTHER PUBLICATIONS

Patent Abstracts of Japan, Publication No. 11-152337, obtained from www19.ipdl.inpit.gojp/PA1, Sep. 30, 2014.*

* cited by examiner

*Primary Examiner* — Porfirio Nazario Gonzalez
(74) *Attorney, Agent, or Firm* — Smith, Gambrell & Russell, LLP

(57) ABSTRACT

The invention relates to a method for preparation of platinum siloxane compounds containing at least one CO ligand molecule (Pt carbonyl siloxanes). The method comprises reacting gaseous carbon monoxide (CO) with a platinum siloxane compound, preferably a platinum vinyl-cyclosiloxane compound, in solution with an organic solvent. The method is straightforward and applicable to industrial scale. With this method, specific isomers of platinum carbonyl vinylcyclosiloxanes are prepared, in which the two η-2-ethenyl groups coordinated to the Pt atom are bonded in trans-configuration relative to the cyclosiloxane backbone. The Pt compounds obtained by the method are used as catalysts for hydrosilylation and for crosslinking and curing of siloxanes and silanes.

22 Claims, 1 Drawing Sheet

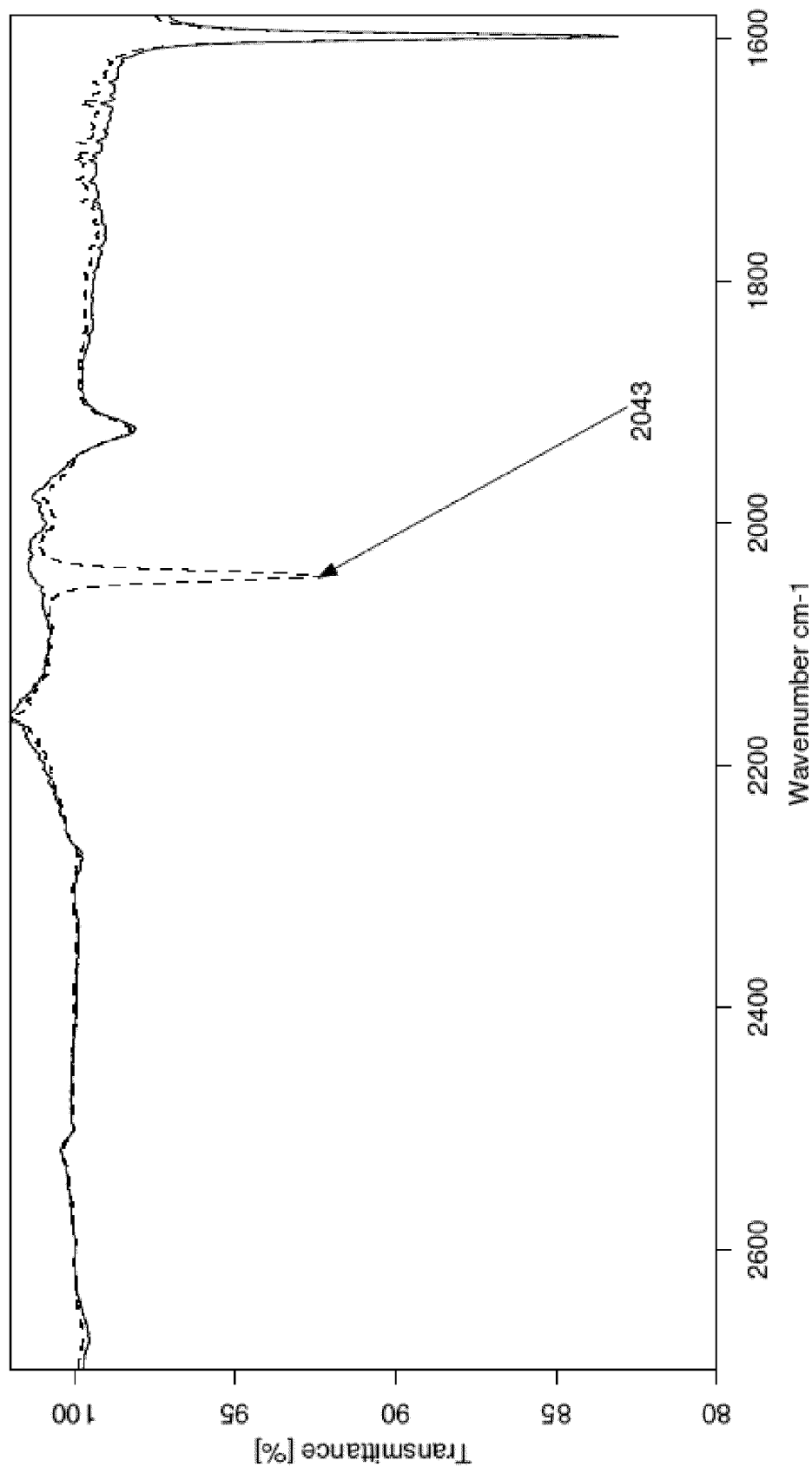

METHOD FOR PREPARATION OF PLATINUM-CARBONYL-SILOXANE COMPOUNDS

FIELD OF INVENTION

The present invention relates to a preparation method for platinum siloxane compounds, in particular to the synthesis of platinum (0) siloxane compounds containing at least one carbon monoxide (CO) ligand bonded to the Pt atom ("Pt carbonyl siloxane" compounds).

BACKGROUND OF THE INVENTION

Siloxanes are chemical compounds composed of units of the form of $R_2SiO$, where R is a hydrogen atom or a hydrocarbon group. They belong to the class of organosilicon compounds. Siloxanes can have branched, unbranched or cyclic backbones consisting of alternating silicon and oxygen atoms [—Si—O—Si—O—], with side chains R attached to the silicon atoms. The word siloxane is derived from the words silicon, oxygen, and alkane.

Polymerized siloxanes with organic side chains (R≠H) are commonly known as silicones or as polysiloxanes. Representative examples are $[SiO(CH_3)_2]_n$ (polydimethylsiloxane) and $[SiO(C_6H_5)_2]_n$ (polydiphenylsiloxane). These compounds can be viewed as a hybrid of both organic and inorganic compounds. The organic side chains confer hydrophobic properties while the —Si—O—Si—O— backbone is purely inorganic.

Hydrosilylation is a reaction widely used in the silicone industry for the preparation of monomers with silicon-carbon bonds and for crosslinking of siloxane compounds. Frequently, vinyl-terminated siloxanes and hydrosiloxanes (i.e. compounds containing a Si—H bond) are reacted in an addition cure mechanism to form siloxane polymers (polysiloxanes). The hydrosilylation and polymerization reactions are catalyzed by highly active platinum catalysts, such as the well-known Karstedt catalyst, which is prepared by the reaction of chloroplatinic acid with divinyl-tetramethyldisiloxane $[CH_2=CH—Si(CH_3)_2—O—Si(CH_3)_2—CH=CH_2]$ in the presence of an alcohol and a base. This catalyst, Pt-divinyl-tetramethyldisiloxane (also abbreviated Pt—VTS) contains Pt in the oxidation state 0 and is commercially available and widely used in the silicone industry, in particular for Pt-catalyzed addition polymerization.

The so-called Ashby catalyst is based on the Pt-tetravinyl-tetramethyl-cyclotetrasiloxane complex and can be depicted by the formula $Pt(CH_2=CH(Me)SiO)_n$ (wherein n=3, 4). This catalyst is commercially available under the name platinum cyclovinylmethylsiloxane complex and is registered under the CAS Registry Nr. 68585-32-0. In the present application, it is hereinafter abbreviated as "Pt—CS".

Only a few Pt siloxane compounds are known, in which carbon monoxide (CO) is bonded directly to the platinum atom.

In U.S. Pat. No. 3,865,858, the reaction products of dicarbonyl-dichloroplatinum $(Pt(CO)_2Cl_2)$ with 2,4,6,8-tetraethenyl-2,4,6,8-tetramethylcyclotetrasiloxane are described. They are used as catalysts for the production of organosilicon compounds.

Further, a compound is commercially available under the name platinum carbonyl cyclovinylmethylsiloxane ("Ossko's catalyst") from different vendors. It is registered as a reaction product of $Pt(CO)_2Cl_2$ with cyclotrisiloxane (ref to CAS Registry No. 73018-55-0). There is no specific formula published for this compound.

The compound platinum carbonyl [2,4-di(η-2-vinyl)-6,8-diethenyl-2,4,6,8-tetramethylcyclotetrasiloxane] is registered under CAS Registry No. 226921-57-9. This compound has the formula $C_{13}H_{24}O_5PtSi_4$ and the structure is given in CAS (Formula I) does not differentiate between stereoisomers. Pt is present as Pt(0) in the oxidation state 0:

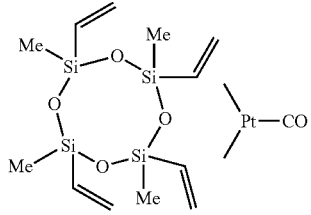

Formula I

In JP2002-30185 a compound is cited with the short formula $Pt(CO)[CH_2=CH(Me)SiO]_4$ under the name Pt(CO)-2,4,6,8-tetraethenyl-2,4,6,8-tetramethyl-cyclotetrasiloxane. JP2002030185 further describes the use of this Pt compound as a catalyst for crosslinking rubber compositions which comprise a Si—H group containing compound and a non-conjugated polyene copolymer. However, no details as to the exact structure and to the preparation process of the Pt-catalyst are given.

CAS Registry Nos. 1269667-88-0 and 1269667-86-8 (registered Mar. 23, 2011) describe Pt carbonyl-tetramethyl-cyclotetrasiloxanes with cis- and trans-configurations of the vinyl groups bonded to the Pt atom.

DETAILED DESCRIPTION OF THE INVENTION

Based on the information given under CAS Registry No. 73018-55-0, the compound $Pt(CO)(CH_2=CH(Me)SiO)_4$ could be prepared by a reaction of Dicarbonyl-dichloroplatinum $(Pt(CO)_2Cl_2)$ with the appropriate vinylmethylcyclosiloxane.

Due to the difficult preparation of the $Pt(CO)_2Cl_2$ starting compound (low yield, product not well defined), this route for the preparation of platinum carbonyl vinylmethylcyclosiloxane is expensive and time consuming.

It was therefore an objective of the present invention to provide an alternative method for the preparation of platinum carbonyl siloxanes, in particular for the preparation of platinum carbonyl vinylcyclosiloxanes.

The new method should be based on readily available starting materials and should be straightforward, easily scalable, environmentally friendly, inexpensive and applicable to industrial scale. In a specific embodiment, the method should be useful for the manufacture of platinum carbonyl vinylcyclosiloxanes, such as Pt(CO)-2,4,6,8-tetraethenyl-2,4,6,8-tetramethyl-cyclotetrasiloxane, hereinafter abbreviated as "Pt—CS—CO".

The present inventors solve this problem by providing the method according to claim 1 and any subsequent claims.

It was found that, in general, CO-containing platinum siloxane complexes (platinum carbonyl siloxanes) can be easily prepared by a treatment of the corresponding cyclic Pt-siloxane compounds with CO gas in a solution with organic solvents.

Thus the present invention provides a method for the preparation of a Pt-carbonyl-siloxane compound comprising at least one CO ligand bonded to the platinum atom and at least one siloxane ligand, wherein gaseous carbon monoxide (CO) is reacted with a Pt-siloxane compound in solution with an organic solvent.

Basically, a broad range of siloxane compounds is suitable for the method of the present invention; however, vinyl-terminated cyclosiloxanes are preferred.

The vinyl-terminated cyclosiloxane is selected from the group consisting of 2,4,6-tri-ethenyl-2,4,6-trimethylcyclotrisiloxane, 2,4,6-tri-ethenyl-2,4,6-triethylcyclotrisiloxane, 2,4,6-tri-ethenyl-2,4,6-tripropylcyclotrisiloxane, 2,4,6-tri-ethenyl-2,4,6-tributylcyclotrisiloxane, 2,4,6-tri-ethenyl-2,4,6-triphenylcyclotrisiloxane, 2,4,6,8-tetra-ethenyl-2,4,6,8-tetramethylcyclotetrasiloxane, 2,4,6,8-tetra-ethenyl-2,4,6,8-tetraethylcyclotetrasiloxane, 2,4,6,8-tetra-ethenyl-2,4,6,8-tetrapropylcyclotetrasiloxane, 2,4,6,8-tetra-ethenyl-2,4,6,8-tetrabutylcyclotetrasiloxane, 2,4,6,8-tetra-ethenyl-2,4,6,8-tetraphenylcyclotetrasiloxane, 2,4,6,8,10-penta-ethenyl-2,4,6,8,10-pentamethylcyclopentasiloxane, 2,4,6,8,10-penta-ethenyl-2,4,6,8,10-pentaethylcyclopentasiloxane, 2,4,6,8,10-penta-ethenyl-2,4,6,8,10-pentapropylcyclopentasiloxane, 2,4,6,8,10-penta-ethenyl-2,4,6,8,10-pentabutylcyclopentasiloxane, 2,4,6,8,10-penta-ethenyl-2,4,6,8,10-pentaphenylcyclopentasiloxane and mixtures and combinations thereof.

In a particularly preferred embodiment, the vinyl-terminated cyclosiloxane ligand is 2,4,6,8-tetra-ethenyl-2,4,6,8-tetramethylcyclotetrasiloxane or 2,4,6-tri-ethenyl-2,4,6-trimethylcyclotrisiloxane or a mixture thereof.

In a still further preferred embodiment, 2,4,6,8-tetraethenyl-2,4,6,8-tetramethyl-cyclotetrasiloxane (hereinafter abbreviated "CS", CAS Registry No. 2554-06-5) is employed as siloxane ligand. In all of these formulas, the "ethenyl" group may also be named "vinyl" group.

As an example, the compound Pt(CO)-2,4,6,8-tetraethenyl-2,4,6,8-tetramethyl-cyclotetrasiloxane, ("Pt—CS—CO") is prepared by a treatment of the cyclic Pt(0) vinylsiloxane compound with CO gas in solution with an organic solvent. It was surprisingly found that this method yields a stereochemically specific Pt siloxane CO adduct, characterized by the trans-configuration of the two (η-2-ethenyl groups bonded to the Pt atom. Accordingly, also the two methyl groups of the siloxane backbone are in trans-position. For the compound Pt(CO)-2,4,6,8-tetraethenyl-2,4,6,8-tetramethyl-cyclotetrasiloxane, this unique stereochemistry is shown in Formula II. To the contrary, the cis-isomer (Formula III) is not formed in the method of the present invention:

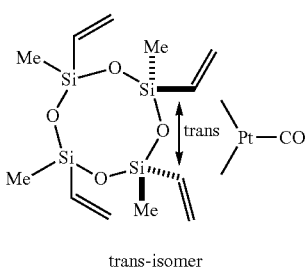

(Formula II)

trans-isomer

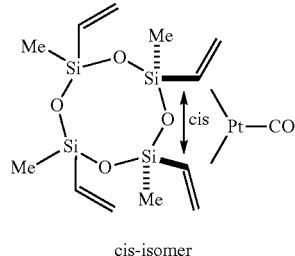

(Formula III)

cis-isomer

The same applies for the analogue compound Pt(CO)-2,4,6-triethenyl-2,4,6-trimethylcyclotrisiloxane, the stereochemistry of the trans-isomer is shown in Formula IV.

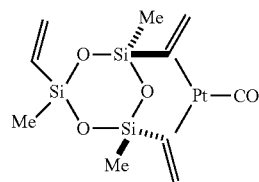

Formula IV

This specific conformation could be a result of the preparation method of the present invention, employing gentle reaction conditions, in particular moderate reaction temperatures, concentrations of reactants and reaction times.

The reaction conditions of the method of the present invention are now described in more detail.

Advantageously in the method of the present invention, the at least one siloxane ligand is employed in excess and acts as the organic solvent for the Pt-siloxane compound: Further, the siloxane ligand may act as a diluent for the reaction and for the final Pt catalyst product. Generally, the Pt-content (by wt.-%) of the Pt-siloxane compound in solution should be in the range of 0.1 to 10 wt.-% Pt, although higher Pt-concentrations (up to 20 wt.-% Pt) are possible. A higher Pt content may lead to reduced stability during CO reaction, causing the reduction and the precipitation of metallic Pt from the solution. Preferably, the Pt-content of the Pt-siloxane starting compound should be in the range of 1 to 5 wt.-% based on the total weight of the solution.

Instead of the siloxane ligand, other organic solvents can be used as solvents and/or diluents for the reaction. Preferred organic solvents are aromatic hydrocarbons, selected from the group consisting of benzene, toluene, the xylene isomers (o-, m- and p-xylene) and mixtures thereof.

The temperature for CO addition should be in the range of 10 to 50° C. Preferably, the CO addition should occur at ambient/room temperature (20-25° C.). The CO addition may be conducted under atmospheric pressure (about 1 bar) or elevated pressure (e.g. in autoclaves, pressure >1.5 bar). In a preferred embodiment, the CO gas is added at atmospheric pressure.

In a particularly preferred version, CO gas is bubbled slowly through a solution of the Pt-siloxane compound in the corresponding siloxane solvent. The addition rate should be between 0.1 to 5 gas bubbles of CO per second. Preferably, the addition rate should be in the range of 0.5 to 2 gas bubbles of CO per second (volume of bubbles in the range of 0.1 to 1 ml). The reaction time for CO addition can be varied in a wide range. Depending of the CO content required, the reaction time may vary between 1 and 20 hours, preferably between 2 and 10 hours.

Generally, the CO content can be monitored by IR spectroscopy during the course of the reaction. For that purpose, an IR spectrum of the reaction medium is taken at the beginning, in the middle and at the end of the CO treatment. CO saturation is achieved, if the intensity (as detected in transmittance (%) of the CO peak in the IR spectrum) is remaining constant. In such saturated state, one CO molecule is attached to one Pt atom (under the hypothesis that only one CO is coordinated to the complex as supported by analysis of the IR spectra).

Thus, the molar ratio of CO to platinum (CO/Pt) typically is in the range of 1:2 to 2:1, preferably in the range of 1:1.2 to 1.2:1. Higher concentrations of CO may lead to instable products and reduced storage stability.

For illustration purposes only, the method of the present invention is described in the following reaction scheme, in which the preparation Pt(CO)-2,4,6,8-tetraethenyl-2,4,6,8-tetramethyl-cyclotetrasiloxane ("Pt—CS—CO") is shown. However, other Pt-siloxane compounds, in particular Pt(CO)-2,4,6-triethenyl-2,4,6-trimethyl-cyclotrisiloxane or mixtures thereof, can be prepared accordingly (Scheme I):

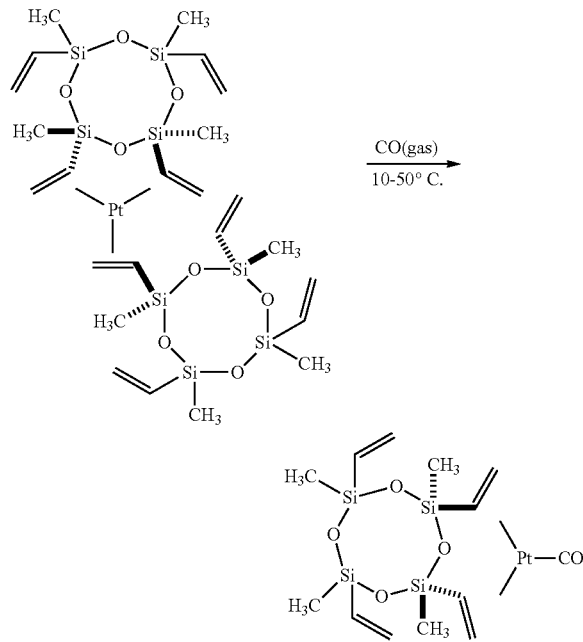

In the reaction, the course of the CO addition reaction is monitored by IR spectroscopy and the amount of CO bonded to the Pt—CS complex is determined by the intensity of the CO band at 2043 cm$^{-1}$ (wavenumber) in the IR spectrum.

In order to confirm that the trans-structure is formed in the reaction products of the present method, theoretical IR and Raman spectra have been calculated by computational techniques and compared with the experimental IR and Raman data of the compound. Such data were based on calculations using density-functional-theory methods (dft), wherein the vibrational modes are based on harmonic oszillator model. As such coordinated C≡O bands, their intensity, form, position and number are subject of symmetry, configuration and conformation of the C≡O complex it should be possible to determine the structure of the new complex.

FIG. 1 provides the IR spectra of Pt—(CO)-2,4,6,8-tetraethenyl-2,4,6,8-tetramethylcyclotetrasiloxane (Pt—CS—CO, dotted line) in comparison with the starting product (Pt—CS, full line). The IR spectrum of the Pt—CO—CS compound shows one single significant C≡O band at 2043 cm$^{-1}$. The corresponding Raman spectrum shows also a single band at 2044 cm$^{-1}$. No additional CO bands are detectable in the region. Thus it can be conducted that only one CO molecule is bonded to each Pt atom. Further, by comparison with the calculated data of the theoretical IR and Raman spectra, the detected C≡O bands can be clearly attributed to the Pt-carbonyl vinylcyclosiloxane isomer, in which the two vinyl groups of the siloxane backbone are in trans-position (ref to Formula II).

By the method of the present invention, Pt carbonyl siloxane compounds are obtained, which are bearing at least one CO ligand bonded to the Pt atom. Preferably, the Pt atom is present as Pt(0) in the oxidation state 0.

The compounds obtained by the present method are useful as catalysts and curing agents for the crosslinking of siloxane and/or silane compounds. In such applications, the use of the Pt catalyst products prepared according to the present method extend the pot life of siloxane formulations and slow down the curing rates. Generally, for certain applications, slow curing rates are advantageous to the user, as they offer a broader process window and higher flexibility in the curing process and manufacture of silicon rubber products.

The invention further refers to the reaction products obtained by the present method, in which the two η-2-ethenyl groups are bonded to the Pt atom in trans-configuration relative to the cyclosiloxane backbone. Examples are:

Platinum carbonyl [2,4-di(η-2-ethenyl)-6,8-diethenyl-2,4,6,8-tetramethyl-cyclotetrasiloxane] and Platinum carbonyl [2,4-di(η-2-ethenyl)-6-ethenyl-2,4,6-trimethyl-cyclotrisiloxane], wherein in both compounds the two η-2-ethenyl groups (vinyl groups) are bonded to the Pt atom in trans-configuration relative to the cyclosiloxane backbone.

Further, the invention refers to a catalyst comprising a mixture of platinum carbonyl [2,4-di(η-2-ethenyl)-6,8-diethenyl-2,4,6,8-tetramethyl cyclotetrasiloxane] and platinum carbonyl [2,4-di(η-2-ethenyl)-6-ethenyl-2,4,6-trimethyl cyclotrisiloxane], wherein in each compound the two η-2-ethenyl groups are bonded to the Pt atom in trans-configuration relative to the cyclosiloxane backbone. Preferably, in the complexes listed above, the Pt atom is present as Pt(0) in the oxidation state 0.

The Pt compounds obtained by the method of the present invention are useful as catalysts for hydrosilylation and for crosslinking and curing of siloxanes.

In particular, it was found that the curing and latency characteristics of the Pt catalyst prepared by the method of the present invention are dependent from the CO content of the Pt catalyst (and thus from the duration of the CO treatment). Depending on the CO content of the Pt—CS—CO catalyst (which is determined by the intensity of the CO peak in the IR spectrum), the latency (pot life) of a specific siloxane formulation can be extended considerably (e.g. from 20 to about 100 minutes; ref to Table 1).

In summary, the method of the present invention is versatile, straightforward and environmentally friendly. As it is based on a simple CO gas treatment of the cyclic Pt siloxane compounds, scale-up to industrial batch sizes is possible without problems.

The following examples are illustrative and may describe the invention in more detail without limiting the scope of the invention.

EXAMPLES

General Comments

The handling of CO should always be conducted under a well ventilated hood. The operator should wear rubber gloves, a face shield and safety glasses whenever working with chemicals. The siloxane starting materials e.g. 2,4,6,8-tetravinyl-2,4,6,8-tetramethylcyclotetrasiloxane or 2,4,6-trivinyl-2,4,6-trimethylcyclotrisiloxane) are available from different vendors (among others: Gelest Inc., USA; Chemos GmbH, Germany).

The preparation of Pt—CS (2,4,6,8-tetravinyl-2,4,6,8-tetramethyl-cyclotetra-siloxane-Pt(0) solution) is conducted according to known literature methods, ref to e.g. U.S. Pat. No. 4,743,377 (to Ashby) and U.S. Pat. No. 3,814,730 (to Karstedt). Generally, Pt—CS is commercially available from different vendors (e.g. product No. PT-50785, Umicore Precious Metals NJ, LLC). Typically, the Pt-content of the commercial products is in the range of 2.0+−0.1 wt.-% Pt. However, products with higher Pt concentrations (2 to 20 wt.-%) are available).

Platinum Catalyst Cure Test:

As small sample (30 g) of a vinyl-terminated dimethylpolysiloxane (Andisil VS1000, Anderson & Ass., Short Hills, N.J.) is thoroughly mixed with 0.11 g of Pt—CS—CO catalyst (2.0 wt.-% Pt). 1.25 g of this premix is combined with 48.75 g of VS1000. To 20 grams of this siloxane formulation, 1.2 g of crosslinker PS123 (silicon-hydride, UCT, Bristol, Pa.) is added. The viscosity of the catalyzed mixture thus obtained is monitored with a Brookfield Viscometer LVTD (Model DV-1) at 25° C. at 0.3 RPM and the initial viscosity is recorded. When the final viscosity of the catalyzed mixture reaches 40.000 cps, the time is recorded again.

The relative cure time is given in minutes; results are shown in Table 1. As a result, with the Pt—CS—CO catalyst prepared according to this invention, the latency period for a two-component polysiloxane composition can be significantly extended. When using the Pt—CS—CO catalyst in the fully saturated stage (highest CO peak intensity in IR), the relative cure time is extended to 98 minutes.

TABLE 1

Cure time of Pt-catalysts vs. CO peak intensity (determined by transmittance [%])

| Pt catalyst | CO peak intensity (IR) transmittance (%) | Relative cure time (mins) |
| --- | --- | --- |
| Pt-CS (neat) | — | 21.9 |
| Pt-CS-CO | 95 | 33.2 |
| Pt-CS-CO | 92 | 98.0 |

Example 1

Preparation of Pt(CO)-2,4,6,8-tetraethenyl-2,4,6,8-tetramethylcyclotetrasiloxane ("Pt—CS—CO")

7.0 lbs (3.175 kg) of Pt—CS (2.0 wt.-% Pt, supplier Umicore, South Plainfield, N.J., USA) are weighed into a 4 liter glass bottle. The bottle is closed with a lid and transported into a well exhausted hood.

A 15 lbs carbon monoxide cylinder is set up in the hood, thereafter a regulator is attached to the top of the cylinder. Attach the end of a plastic disposable pipette at the end of the CO hose with a hose clamp. The lid of the glass bottle is removed and the pipette is secured in the bottle using a twist tie. The valve of the CO cylinder is opened and the CO flow is reduced until there is only a slow bubbling (approx. 1 bubble per second). The reaction is examined by IR spectroscopy. The IR spectrum shows a single significant C═O band at 2043 $cm^{-1}$. After one, four and six hours of CO bubbling, the solution is checked by IR spectroscopy. After eight hours of CO bubbling at room temperature, the intensity of the CO-peak remains constant. The pipette is removed from the solution and the lid is replaced on the glass bottle. The glass bottle is finally purged with nitrogen. For comparison, the non-CO containing Pt—CS starting compound is examined as well and does not show any band in the region of 2000 to 2200 $cm^{-1}$ (ref to FIG. 1).

Based on computational studies on the theoretical calculation of IR and Raman spectra it is shown that in the resulting Pt—CS—CO complex only one CO molecule is coordinated to the Pt atom. Further, the complex is present as trans-isomer, wherein the coordinated two vinyl groups of the cyclosiloxane backbone are bonded in trans-configuration. The Pt content is 2.0+−0.1 wt.-%.

Example 2

Preparation of Pt(CO)-2,4,6,8-tetraethenyl-2,4,6,8-tetramethylcyclotetrasiloxane ("Pt—CS—CO") in CS/xylene solution 1.10 lbs (0.5 kg) of Pt—CS (15.0 wt.-% Pt, supplier Umicore, South Plainfield, N.J., USA) are weighed into a 4 liter glass bottle. 3.31 lbs (1.5 kg) of 2,4,6,8-tetraethenyl-2,4,6,8-tetramethylcyclotetrasiloxane (CS) and 2.75 lbs (1.25 kg) of xylene are added and the final solution is mixed to result in a 2.0 wt.-% Pt solution. The bottle is closed with a lid and transported into a well exhausted hood.

A 15 lbs carbon monoxide cylinder is set up in the hood, thereafter a regulator is attached to the top of the cylinder. Attach the end of a plastic disposable pipette at the end of the CO hose with a hose clamp. The lid of the glass bottle is removed and the pipette is secured in the bottle using a twist tie. The valve of the CO cylinder is opened and the CO flow is reduced until there is only a slow bubbling (approximately 1 bubble per second). After one hour of CO bubbling, the solution is checked. After 8 hours of CO bubbling at room temperature, the pipette is removed from the solution and the lid is replaced on the glass bottle. The obtained product is examined by IR spectroscopy. The Pt content is 2.0+−0.1 wt.-%.

The invention claimed is:

1. A method for the preparation of a Pt-carbonyl-siloxane compound comprising at least one CO ligand bonded to the platinum atom and at least one siloxane ligand, wherein gaseous carbon monoxide (CO) is reacted with a Pt-siloxane compound in solution with an organic solvent.

2. The method according to claim 1, wherein the siloxane ligand is a vinyl-terminated cyclosiloxane.

3. The method according to claim 1, wherein the siloxane ligand is selected from the group consisting of 2,4,6-tri-ethenyl-2,4,6-trimethylcyclotrisiloxane, 2,4,6-tri-ethenyl-2,4,6-triethylcyclotrisiloxane, 2,4,6-tri-ethenyl-2,4,6-tripropylcyclotrisiloxane, 2,4,6-tri-ethenyl-2,4,6-tributylcyclotrisiloxane, 2,4,6-tri-ethenyl-2,4,6-triphenylcyclotrisiloxane, 2,4,6,8-tetra-ethenyl-2,4,6,8-tetramethylcyclotetrasiloxane, 2,4,6,8-tetra-ethenyl-2,4,6,8- tetraethylcyclotetrasiloxane, 2,4,6,8-tetra-ethenyl-2,4,6,8-tetrapropylcyclotetrasiloxane, 2,4,6,8-tetra-ethenyl-2,4,6,8-tetrabutylcyclotetrasiloxane, 2,4,6,8-tetra-ethenyl-2,4,6,8-tetraphenylcyclotetrasiloxane, 2,4,6,8,10-penta-ethenyl-2,4,6,8,10-pentamethylcyclopentasiloxane, 2,4,6,8,10-penta-ethenyl-2,4,6,8,10-pentaethylcyclopentasiloxane, 2,4,6,8,10-penta-ethenyl-2,4,6,8,10-pentapropylcyclopentasiloxane, 2,4,6,8,10-penta-ethenyl-2,4,6,8,10-pentabutylcyclopentasiloxane, 2,4,6,8,10-penta-ethenyl-2,4,6,8,10-pentaphenylcyclopentasiloxane and mixtures and combinations thereof.

4. The method according to claim 1, wherein the siloxane ligand is 2,4,6,8-tetra-ethenyl-2,4,6,8-tetramethylcyclotetrasiloxane or 2,4,6-tri-ethenyl-2,4,6-trimethylcyclotrisiloxane or a mixture thereof.

5. The method according to claim 1, wherein the Pt content of the platinum-siloxane compound is in the range of 0.1 to 10 wt-% Pt.

6. The method according to claim 1, wherein the reaction time for CO addition is in the range of 1 to 20 hours.

7. The method according to claim 1, wherein the reaction temperature is in the range of 10 to 50° C.

8. The method according to claim 1, wherein the CO addition is conducted by bubbling at atmospheric pressure or under elevated pressure.

9. The method according to claim 1, wherein the at least one siloxane ligand employed is used as organic solvent.

10. The method according to claim 1, wherein an aromatic hydrocarbon solvent selected from the group consisting of benzene, toluene, o-, m- or p-xylene or mixtures thereof is used as organic solvent.

11. The method according to claim 1, wherein a mixture of the at least one siloxane ligand and an aromatic hydrocarbon solvent is used as solvent.

12. The method according to claim 1, wherein the molar ratio of Pt/CO is in the range of 1:2 to 2:1.

13. Platinum carbonyl [2,4-di(η-2-ethenyl)-6,8-diethenyl-2,4,6,8-tetramethyl-cyclotetrasiloxane] according to Formula II

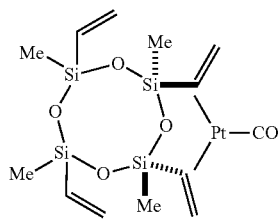

Formula II wherein the two η-2-ethenyl groups are bonded to the Pt atom in trans-configuration relative to the cyclosiloxane backbone.

14. Platinum carbonyl [2,4-di(η-2-ethenyl)-6-ethenyl-2,4,6-trimethylcyclotri-siloxane] according to Formula IV

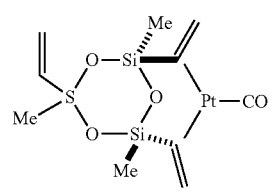

Formula IV wherein the two η-2-ethenyl groups are bonded to the Pt atom in trans-configuration relative to the cyclosiloxane backbone.

15. Catalyst comprising a mixture of platinum carbonyl [2,4-di(η-2-ethenyl)-6,8-diethenyl-2,4,6,8-tetramethyl cyclotetrasiloxane] and platinum carbonyl [2,4-di(η-2-ethenyl)-6-ethenyl-2,4,6-trimethyl cyclotrisiloxane], wherein in each Pt compound the two η-2-ethenyl groups are bonded to the Pt atom in trans-configuration relative to the cyclosiloxane backbone.

16. A method for hydrosilylation, comprising utilizing the compounds according to claim 13 as a catalyst in the hydrosilylation.

17. A method for crosslinking and curing of siloxanes, comprising utilizing the compounds according to claim 13 as a catalyst for the crosslinking and curing of the siloxanes.

18. A method for hydrosilylation, comprising utilizing the compound according to claim 14 as a catalyst in the hydrosilylation.

19. A method for crosslinking and curing of siloxanes, comprising utilizing the compound according to claim 14 as a catalyst for the crosslinking and curing of the siloxanes.

20. A method for hydrosilylation, comprising utilizing the compound according to claim 15 as a catalyst in the hydrosilylation.

21. A method for crosslinking and curing of siloxanes, comprising utilizing the compound according to claim 15 as a catalyst for the crosslinking and curing of the siloxanes.

22. The method according to claim 1, wherein the molar ratio of Pt/CO is in the range of 1:1.2 to 1.2:1.

* * * * *